(12) United States Patent
Shidara et al.

(10) Patent No.: US 8,372,458 B2
(45) Date of Patent: Feb. 12, 2013

(54) CONTINUOUS EMULSIFICATION PROCESS FOR PROCESS CHEESE TYPE AND EQUIPMENT THEREFOR, AND CONTINUOUS PRODUCTION METHOD FOR PROCESS CHEESE TYPE AND EQUIPMENT THEREFOR

(75) Inventors: Hideo Shidara, Tokyo (JP); Junichi Otsuji, Tokyo (JP); Kiyotaka Takahashi, Ebina (JP); Takeshi Goto, Sagamihara (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 605 days.

(21) Appl. No.: 12/616,353

(22) Filed: Nov. 11, 2009

(65) Prior Publication Data
US 2010/0055288 A1 Mar. 4, 2010

Related U.S. Application Data

(62) Division of application No. 10/526,988, filed as application No. PCT/JP2004/009869 on Jul. 5, 2004, now Pat. No. 7,637,207.

(30) Foreign Application Priority Data

Jul. 10, 2003 (JP) ................................ 2003-273068

(51) Int. Cl.
*A23C 19/08* (2006.01)
(52) U.S. Cl. ........ 426/231; 426/582; 426/519; 426/521; 426/634
(58) Field of Classification Search ............. 99/348, 99/452, 483, 484, 352, 353, 354, 355, 509; 426/634, 656, 518, 486, 507, 231, 582, 519, 426/521
See application file for complete search history.

(56) References Cited

U.S. PATENT DOCUMENTS
(Continued)

FOREIGN PATENT DOCUMENTS
DE 4423988 A1 1/1996
JP 3-295442 A 12/1991
(Continued)

OTHER PUBLICATIONS
Official Action issued in European Patent Application No. 04747337.6, dated Jul. 13, 2011, 3 pages.
(Continued)

*Primary Examiner* — Reginald L Alexander
(74) *Attorney, Agent, or Firm* — Wood, Herron & Evans, L.L.P.

(57) ABSTRACT

Objects of the present invention are to provide a continuous emulsification process and equipment therefor in which exact viscosity is measured inline and production conditions are controlled automatically, and a continuous production method for process cheese type and equipment therefor. The present invention provides a continuous production method for process cheese type in which process cheese type ingredients are agitated and emulsified with any agitation intensity by an agitation bar 4 while heating in the vessel which is applied with fixed back pressure, the process cheese type is flowed and held in a holding pipe 7 for a certain period and thereby the process cheese type is cooled, and then the cooled process cheese type is molded and filled and a process cheese type product 13 is produced, wherein a transducer of an oscillating viscometer is immersed in the process cheese type during holding or after cooling such that the transducer is not directly contacted with the process cheese type; and wherein agitation intensity of the agitation device and/or back pressure applied to the vessel is adjusted such that a detected value of the transducer becomes near a target value which is set in advance, and thereby production conditions are controlled automatically so that the viscosity of the process cheese type during holding or after cooling becomes near a target viscosity.

2 Claims, 1 Drawing Sheet

U.S. PATENT DOCUMENTS

| | | | |
|---|---|---|---|
| 4,811,593 | A | 3/1989 | Miura et al. |
| 5,228,331 | A | 7/1993 | Odagiri et al. |
| 5,621,165 | A | 4/1997 | Miura et al. |
| 5,853,786 | A | 12/1998 | Anbarci et al. |
| 6,331,324 | B1 | 12/2001 | Tomita et al. |
| 6,672,140 | B2 | 1/2004 | Miura |
| 7,147,886 | B2 | 12/2006 | Kikuchi et al. |

FOREIGN PATENT DOCUMENTS

| | | |
|---|---|---|
| JP | 6-25729 | 7/1992 |
| JP | 4-304843 | 10/1992 |
| JP | 5-20692 | 3/1993 |
| JP | 5-277991 | 10/1993 |
| JP | 8-30674 | 2/1995 |
| JP | 2622361 | 4/1996 |
| JP | 8-140572 | 6/1996 |
| JP | 8-266222 A | 10/1996 |
| JP | 9-502886 A | 3/1997 |
| JP | 11-221016 | 8/1999 |
| JP | 3348162 | 11/2001 |
| JP | 2005-229825 | 9/2005 |
| WO | 96/01567 | 1/1996 |

OTHER PUBLICATIONS

The International Bureau of WIPO, International Search Report, dated May 2004.
Australian Government, IP Australia, report No. 2 on patent application No. 20044255084, dated Oct. 19, 2006, 2 pgs.
Polytetrafluoroethylene, Wikipedia encyclopedia, http://en.wikipedia.org/wiki/Teflon, dated Oct. 24, 2006, 5 pgs.
Wayne L. Chandler and Gottfried Schmer, Evaluation of a New Dynamic Viscometer for Measuring the Viscosity of Whole Blood and Plasma, Clinical Chemistry, vol. 32, No. 3, 1986, pp. 505-507.
Japanese Patent Office, Notice of Reasons for Rejection, Application No. 2005-511553, dated Jun. 26, 2007.

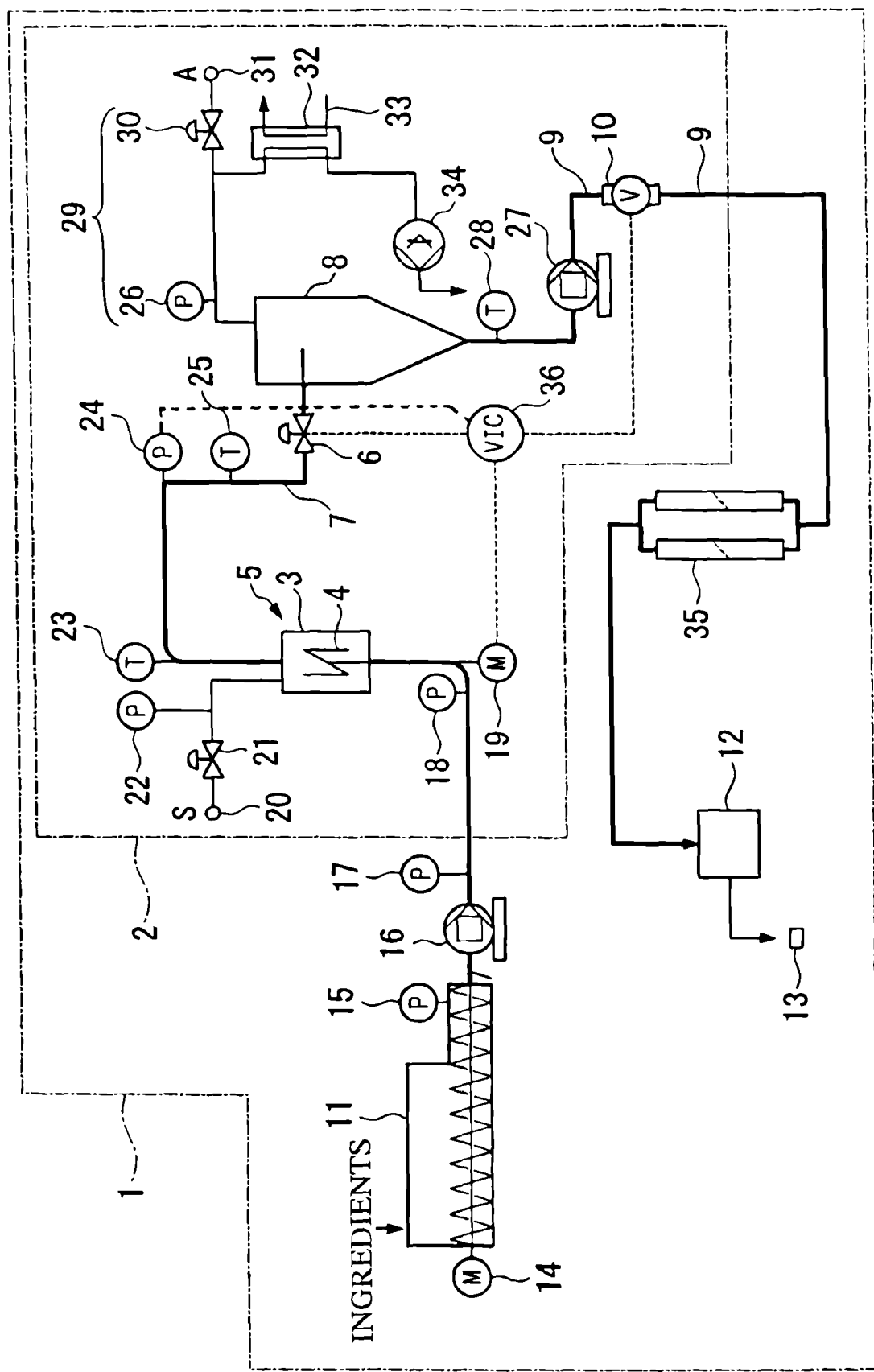

CONTINUOUS EMULSIFICATION PROCESS FOR PROCESS CHEESE TYPE AND EQUIPMENT THEREFOR, AND CONTINUOUS PRODUCTION METHOD FOR PROCESS CHEESE TYPE AND EQUIPMENT THEREFOR

CROSS REFERENCE TO RELATED APPLICATIONS

This application is a Divisional of U.S. patent application Ser. No. 10/526,988 entitled "CONTINUOUS EMULSIFICATION PROCESS FOR PROCESS CHEESE TYPE AND EQUIPMENT THEREFOR, AND CONTINUOUS PRODUCTION METHOD FOR PROCESS CHEESE TYPE AND EQUIPMENT THEREFOR" filed Mar. 7, 2005 (pending), which is a U.S. National Phase under 35 U.S.C. 371 of International Application PCT/JP2004/009869 filed Jul. 5, 2004, which claims priority to Japanese Patent Application No. 2003-273068 filed Jul. 10, 2003, the disclosures of which are hereby incorporated by reference herein.

TECHNICAL FIELD

The present invention relates to a continuous emulsification process for heating and emulsifying process cheese type and equipment therefor, and to a continuous production method for process cheese type and equipment therefor.

In the present invention, "process cheese type" includes, for example, products produced by a production method in which food containing cheese such as food containing cheese food, cheese as a primary ingredient is subjected to heat emulsification similarly in process cheese, other than process cheese defined in ministerial ordinance (Promulgated in Dec. 27, 1951, Ministry of Health and Welfare, Announcement No. 52). However, process cheese, which is defined in this ministerial ordinance, is most preferably used in the present invention.

Priority is claimed on Japanese Patent Application No. 2003-273068, filed Jul. 10, 2003, the content of which is incorporated herein by reference.

BACKGROUND ART

Process cheese is produced by crushing cheese ingredients such as natural cheese, heating and melting, and then emulsifying (this is defined in the above-mentioned ministerial ordinance). In a continuous production method for process cheese type, these processes are continuously performed.

For example, Published Japanese Translation No. H9-502886 of the PCT International Publication suggests a continuous production method for process cheese in which a process a) for preparing substantial homogeneous cooked liquid materials flow from cheese ingredients needed to obtain cheese products, a process b) for heat treating the cooked liquid materials flow, if necessary, a process c) for cooling the cooked liquid materials flow to a temperature suitable for an adjustment of the viscosity thereof, if necessary, a process d) for circulating all or apart of the cooked liquid materials flow in a closed circulation system at least at the beginning of this process and shear stress is applied to the cooked liquid material flow to adjust the viscosity thereof to a desirable value, and a process e) for taking out the cooked liquid materials flow from the closed circulation system and after any other desired treatments and/or a temporary storage, the cooked liquid materials are taken out as a final product.

In addition, for example, Japanese Unexamined Patent Application, First Publication No. H11-221016 suggests process cheese having suitable flow property which is heated in an electric oven, and contains moisture in a range from 43 to 55% by weight and fat in a range from 59 to 75% by weight in a solid content, and which has a viscosity in a range from 500 to 1,500 cP at 70° C. (measured by an oscillating viscometer).

The oscillating viscometer, for example, is disclosed in Japanese Examined Patent Applications, First Publications Nos. H5-20692, H6-25729, and H8-30674, and Japanese Patent (Granted) Publications Nos. 2622361 and 3348162.

In production processes for process cheese type, properties of melted cheese vary depending on several factors such as kinds, maturation degree, composition, melting condition strongly influences processes after melting of cheese and quality of products, it is important to adjust melting conditions and thereby to stabilize the viscosity of the melted cheese. However, online measurement of the viscosity of melted cheese is difficult, and in the past, the viscosity of melted cheese is visual evaluated by an operator or measured by an offline viscometer for convenience, However, the viscosity of melted cheese is not measured visually. In addition, when a part of melted cheese is picked up from a production line and the viscosity of the cheese is measured by an offline viscometer, since time is needed for the measurement, a problem of a time lag, in which melted cheese is transferred to a next process during measurement, arises. Therefore, it is difficult to suitably adjust and control automatically the production conditions based on offline measurement data.

Many online viscometers have been used and measurement of agitation torque, pressure drop during transfer of melted cheese, and the like have been measuring to evaluate the viscosity of melted cheese. For example, Published Japanese Translation No. H9-502886 of the PCT International Publication estimates the viscosity based on pressure drop measured by a built-in online measuring device. In Japanese Unexamined Patent Application, First Publication No. H11-221016, the end of a probe of an oscillating viscometer is contacted with process cheese and thereby the viscosity thereof is measured.

However, among conventional viscosity measuring methods, a method, in which the viscosity of process cheese is estimated based on pressure drop during transfer of melted cheese or agitation torque, does not readily measure an exact viscosity. When process cheese type is produced by controlling production conditions based on such inexact viscosity, there is a possibility that process cheese having desired quality is not produced (For example, please refer a following Comparative Example).

In addition, when an attempt is made to measure the viscosity of melted cheese using an online oscillating viscometer having a transducer (probe), since cheese adheres to the transducer (probe) and measurement of the viscosity is impossible, it is very difficult to online measure the viscosity of melted cheese.

In consideration of the above-described problems, an object of the present invention is to provide a continuous emulsification process for heating and emulsifying process cheese type continuously in which the accurate viscosity measured inline is obtained and production conditions are controlled automatically and equipment therefore, and a continuous production method for process cheese type and equipment therefor.

DISCLOSURE OF INVENTION

In order to achieve the objects, the present invention provides a continuous emulsification process for process cheese type in which a series is continuously conducted, which comprises a heating process for agitating and emulsifying process cheese type at any agitation intensity using an agitation device provided in a vessel while the process cheese type is heated in the vessel applied with certain back pressure, a holding process for holding the heated process cheese type for a fixed time while the heated process cheese is flowed into a pipe, and a cooling process for cooling the held process cheese, wherein a transducer of an oscillating viscometer is immersed in the process cheese type in the holding process or after the cooling process such that the transducer is not directly contacted with the process cheese type; and wherein agitation intensity of the agitation device and/or back pressure applied to the vessel in the heating process is adjusted such that a detected value of the immersed transducer becomes near a target value which is set in advance, and thereby, production conditions are controlled automatically and the process cheese type is emulsified such that the viscosity of the process cheese in the holding process or after cooling process becomes near a target viscosity.

In the continuous emulsification process for process cheese type, it is preferable that when the transducer of the oscillating viscometer is immersed in the process cheese type, the transducer be coated with a coating material in advance so as not to contact directly the process cheese type.

In addition, the present invention also provides a continuous production method for process cheese type in which process cheese ingredients are kneaded, the kneaded process cheese type ingredients are transferred to a vessel applied with certain back pressure, and the process cheese type is agitated and emulsified with any agitation intensity using an agitation device provided in the vessel while heating in the vessel, the heated process cheese type is held by flowing in a pipe for a certain period, the held process cheese type is cooled, and the cooled process cheese type is molded and filled and a process cheese type product is produced, wherein a transducer of an oscillating viscometer is immersed in the process cheese type during holding or after cooling such that the transducer is not directly contacted with the process cheese type; and wherein agitation intensity of the agitation device and/or back pressure applied to the vessel during heating is adjusted such that a detected value of the immersed transducer becomes near a target value which is set in advance, and thereby, production conditions are controlled automatically so that the viscosity of the process cheese type during holding or after cooling becomes near a target viscosity.

In the continuous production method for process cheese type, it is preferable that when the transducer of the oscillating viscometer is immersed in the process cheese type, the transducer be coated with a coating material in advance so as not to contact directly the process cheese type.

In addition, the present invention provides a continuous emulsification equipment for process cheese type comprising a heating equipment comprising a heating device for heating process cheese type and an agitation device for agitating the process cheese type at any agitation intensity, a holding pipe one end of which is connected to an outlet of the heating equipment and a back pressure regulating valve is provided, a cooling device for cooling the process cheese type which is connected to the end of the holding pipe, and a carrying out pipe for carrying the process cheese type which is already emulsified, one end of which is connected to an outlet of the cooling device, wherein an oscillating viscometer comprising a transducer is provided to the holding pipe or the carrying out pipe, wherein the transducer of the oscillating viscometer is immersed in the process cheese type flowing in the holding pipe or the carrying out pipe such that the transducer is not directly contacted with the process cheese type; and wherein an output line for outputting detected values by the immersed transducer is connected to a display device, a recording device, and/or a printing device.

In the continuous emulsification equipment for process cheese type, it is preferable to comprise a control equipment for controlling automatically agitation intensity of the agitation device and/or opening of the back pressure regulating valve such that the detected values of the transducer becomes near a target value which is set in advance.

In addition, it is also preferable for the transducer of the oscillating viscometer to be coated with a coating material. Furthermore, the coating material is preferably made of fluorocarbon resin.

In addition, the present invention provides a continuous production equipment for process cheese type comprising a kneader for kneading process cheese type ingredients, the continuous emulsification equipment, and molding and filling equipment for molding and filling the process cheese type which is sent through the carrying out pipe of the continuous emulsification equipment and thereby a process cheese type produce is produced.

BRIEF DESCRIPTION OF THE DRAWINGS

FIG. 1 is a block diagram of one embodiment of the continuous production equipment according to the present invention.

MODES FOR CARRYING OUT THE INVENTION

Below, preferred embodiments of the present invention will be explained with reference to the figure. However, the present invention is not limited to the following embodiments.

FIG. 1 shows one embodiment of a continuous production equipment 1 and a continuous emulsification equipment 2 for process cheese type of the present invention.

The continuous production equipment 1 comprises an auger screw kneading machine 11 for kneading process cheese type ingredients, a continuous emulsification equipment 2, and a molding and filling equipment 12 for molding and filling process cheese type which is sent thereto through a carrying out pipe 9 of the continuous emulsification equipment 2 and producing a process cheese type product 13.

The continuous emulsification equipment 2 comprises mainly a heating equipment 5 for heating and agitating process cheese type, a holding pipe 7, one end of which is connected to an outlet of the heating equipment 5 and a back pressure regulating valve 6 is provided, a cooling chamber 8 (cooling device) which is connected to the end of the holding pipe 7, a carrying out pipe 9 for carrying out process cheese type which is already emulsified, one end of which is connected to an outlet of the cooling chamber 8, an oscillating viscometer 10 which is provided with the carrying out pipe 9 and which measures the viscosity of process cheese type flowing in the carrying out pipe 9 by a transducer immersed in the process cheese type so as not to directly contact the process cheese type, and a control equipment 36 for controlling automatically output of a frequency controlled variable speed drive 19 for agitating in the heating equipment 5 and opening of the back pressure regulating valve 6 such that detected values of the transducer of the oscillating viscometer 10 becomes near a target value which is set in advance.

The auger screw kneading machine 11 comprises a main body having an inlet of the ingredients and an outlet of the mixed materials and a screw in the main body which rotates by a motor 14. When a fixed amount of various cheese ingredients are introduced into the auger screw kneading machine 11 from the inlet by driving the motor 14, the cheese ingredients are transferred to the vent while kneading, and a mixed material, in which each cheese ingredients are uniformly dispersed, is supplied continuously. A pressure gauge 15 is provided near the vent. Cheese ingredients, which are taken out from the vent, is supplied to the heating equipment 5 of the continuous emulsification equipment 2 by a metering pump 16. A pipe between the metering pump 16 and the heating equipment 5 is provided with pressure gauges 17 and 18.

The heating equipment 5 of the continuous emulsification equipment 2 comprises a vessel 3 having an inside which can be pressurized by applying back pressure by a back pressure regulating valve 6, an agitation bar 4 (agitation device) which is provided rotatably inside of the vessel 3, a frequency controlled variable speed drive 19 for rotating the agitation bar 4, and a steam source 20 which supplies steam into the vessel 3 through a steam supply pipe comprising a control valve 21 and a pressure gauge 22. The frequency controlled variable speed drive 19 for rotating the agitation bar 4 in the vessel 3 is connected to the control equipment 36, and thereby revolution of the agitation bar 4 is controlled by an output signal from the control equipment 36.

In the present invention, a method for supplying heat to heat process cheese type is not limited. In general, continuous emulsification equipments are classified into a direct type and an indirect type based on a heating method. In the direct type continuous emulsification equipment, steam is blown to cheese and the cheese is heated, after that, the steam is removed from the cheese in the cooling chamber 8 by boiling and the cheese is cooled. In the indirect type continuous emulsification equipment, using a heat exchanger, cheese is heated and cooled by a heat transfer wall. In this case, the heat exchanger includes a plate heat exchanger, a tube heat exchanger, a scraped surface heat exchanger, and the like. In the heating equipment 5 of the continuous emulsification equipment 2 of the present embodiment, the direct type, in which steam is blown to the vessel 3 containing cheese and the cheese is directly heated, is adopted. In FIG. 1, the vessel 3 is drawn so as to have a tank shape having a diameter which is larger than the diameter of pipes connected to the vessel 3 from the upstream and downstream. However, the vessel 3 may have a diameter which equals to or is smaller than the diameter of the pipes. That is, the heating equipment 5 includes an embodiment in which steam is blown to simple pipes and cheese is directly heated.

The holding pipe 7 for sending the process cheese type which is heated and agitated in the heating equipment 5 to the cooling chamber 8 comprises the back pressure regulating valve 6, and thermometers 23 and 25, and pressure gauge 25 at the upstream relative to the back pressure regulating valve 6. The opening of the back pressure regulating valve 6 is adjusted by a signal from the control equipment 36, and thereby back pressure applied to the vessel 3 of the heating equipment 5 is adjusted.

The cooling chamber 8 adopts a boiling evaporation type cooling device such as a flash vessel in which the process cheese type sent through the holding pipe 7 is introduced into a room under a vacuum ambience, moisture content is evaporated and thereby the process cheese type is cooled. Moreover, when the heating method is a direct heating method, a heat exchanger and the like is used as a cooling device.

With the bottom of the cooling chamber 8, one end of the carrying out pipe 9 for carrying out the cooled process cheese type is provided. The carrying out pipe 9 is provided with a thermometer 28, a metering pump 27, an oscillating viscometer 10, and a filter 35. With the top of the cooling chamber 8, a vacuum exhaust line 29 for maintaining the inside of the cooling chamber 8 at a vacuum ambient is provided. The vacuum exhaust line 29 comprises a vacuum pump 34, a pressure gauge 26 which is provided with pipe connecting between the top of the cooling chamber 8 and the vacuum pump 34, a pressure-regulating valve 30 which has one end connecting an air supply 31, and a condenser 32 for condensing steam discharged from the cooling chamber 8. The condenser 32 is connected with a cooling water feed pipe 33.

The oscillating viscometer 10 provided with the carrying out pipe 9 comprises the transducer which is immersed in the process cheese so as not to contact directly the process cheese. In the present invention, an oscillating viscometer 10, which can measure the viscosity of process cheese type via the transducer, is used. Main structure and measuring principle of the oscillating viscometer 10 are disclosed, for example, in Japanese Examined Patent Applications, First Publication Nos. H5-20692, H6-25729, and H8-30674, and Japanese Patent (Granted) Publications Nos. 2622361 and 3348162. However, when the oscillating viscometer disclosed in such documents is used to measure online directly the viscosity of melted process cheese, process cheese adheres to the transducer, and the viscosity of melted process cheese is not measured. Therefore, in the present invention, the transducer is coated with fluorocarbon resin such as polytetrafluoroethylene, and direct contact between process cheese type and the transducer is prevented and adhesion of process cheese type to the transducer is prevented, and thereby measurement of the viscosity of process cheese type is made possible.

A method for coating the transducer with a coating material includes a method in which the transducer is coated with a lamina (coating material) made of fluorocarbon resin, and a method in which the transducer is put into a mold form (coating material) made of fluorocarbon resin. The former is simple but there is a possibility that the lamina made of fluorocarbon resin will peel off from the transducer after long use. Therefore, when the durability is concerned, the latter is preferable.

In principle, the oscillating viscometer 10 measures the value of density×viscosity. Since the density of cheese does not substantially vary depending on time, the measurement of the oscillating viscometer 10 equals the measurement of the viscosity of process cheese type. It is also possible to measure separately the density using an offline or another online densimeter, and thereby accurate density is calculated.

The control equipment 36 may be a computer comprising a central processing unit (CPU), a memory equipment such as a hard disc drive, an input device such as a keyboard, and a display device such as a monitor, and the like. To the control equipment 36, an output line of the oscillating viscometer 10 is connected. In addition, in order to control one or both of the frequency controlled variable speed drive 19 of the heating equipment 5 and the back pressure regulating valve of the holding pipe 7, the control equipment 36 is connected to them. The output of the oscillating viscometer 10 is input in the control equipment 36, and the output is checked by the display device such as a monitor and the like which is provided with the control equipment 36.

According to the size (contents quantity), shape, and packaging style of process cheese type product 13 to be produced, conventional various molding and filling equipment which have been used for producing process cheese type can be used as the molding and filling equipment 12.

In FIG. 1, the oscillating viscometer 10 is provided with the carrying out pipe 9; however, the oscillating viscometer 10 may be provided with the holding pipe 7. When the oscillating viscometer 10 is provided with the holding pipe 7, the viscosity of process cheese type can be measured similarly in the case of the oscillating viscometer 10 provided with the carrying out pipe 9. However, since the temperature of the holding pipe 7 becomes high, if anything, it is preferable for the oscillating viscometer 10 to be provided with the carrying out pipe 9.

Below, the continuous emulsification process and the continuous production method for process cheese type according to the present invention will be explained. The continuous emulsification process is a main step of the continuous production method. The continuous emulsification process continuously performs a series of a heating process for heating, agitating, and emulsifying process cheese type in the vessel 3 applied with certain back pressure, a holding process for holding the heated process cheese type for a fixed time while the heated process cheese is flowed into the holding pipe 7, and a cooling process for cooling the held process cheese. The continuous production method comprises a process for kneading process cheese ingredients and transferring the kneaded cheese ingredients to the vessel 3, and a process for molding and filling the process cheese type produced by the continuous emulsification process and thereby a process cheese type product 13 is produced, in addition to the each process of the continuous emulsification process. The continuous production method for process cheese type according to the present invention is preferably performed by the continuous production equipment 1 shown in FIG. 1.

The ingredients of process cheese type are put into the auger screw kneading machine 11 from the inlet, and dispersed uniformly therein 11. The ingredients of process cheese type include ingredients used in conventional productions for process cheese such as cheese ingredients, water, precooked cheese, pH adjusters, fat ingredients, milk protein ingredients, spices, nuts, seasoning foods, flavors, colorants, preservatives, stabilizers, and emulsifiers. The cheese ingredients include semi-hard or hard cheese such as Cheddar cheese, Gouda cheese, and Emmental cheese, and soft cheese such as Cream cheese, Blue cheese, and Camembert cheese. If necessary, a plurality of them may be combined.

The kneaded cheese ingredients are transferred to the vessel 3 of the heating equipment 5 by the metering pump 16, and agitated and emulsified by the agitation bar 4 in the vessel 3 at any agitation intensity while the process cheese type is heated in the vessel 3 applied with certain back pressure. The conditions of the heating process are set depending on kinds of cheese ingredients, a compounding ratio, a water amount, and the like. In general, a heating temperature is in a range from 70 to 140° C., a pressure (back pressure) in the vessel is in a range from 0 to 500 kPa, and a revolution of the agitation bar 4 is in a range from 300 to 1,500 rpm.

The process cheese type, which is emulsified in the vessel 3, is held for a fixed time by flowing into the holding pipe 7, after that, the process cheese type is sent to the cooling chamber 8 under a vacuum ambience. In the cooling chamber 8, a part of moisture in the process cheese type evaporates, and the temperature of the process cheese type decreases. The holding time in the holding pipe 7 is usually in a range from about 2 to 30 seconds. The pressure in the cooling chamber 8 is usually in a range from about 0 to −70 kPa. The moisture discharged from the top of the cooling chamber 8 is condensed in the condenser 32, and then discharged. The process cheese type, which is taken from the bottom of the cooling chamber 8, passes through the metering pump 27 and flows in the carrying out pipe 9, and then contacts the coating material of the transducer of the oscillating viscometer 10 in the way to the filter 35, and thereby the viscosity of the process cheese type is measured. The output of the oscillating viscometer 10 is sent to the control equipment 36.

After measuring the viscosity in the oscillating viscometer 10, the process cheese type passes through the filter 35, and is sent to the molding and filling equipment 12. In the molding and filling equipment 12, the process cheese type is molded in a desired shape and size (content quantity), and packaged into a desired packaging style to produce a process cheese type product 13.

In the present invention, the oscillating viscometer 10 may be provided with the carrying out pipe 9 or the holding pipe 7. When the oscillating viscometer 10 is provided with the carrying out pipe 9, the oscillating viscometer 10 measures the viscosity of the process cheese type which is just cooled in the cooling chamber 8 (that is, after the cooling process). When the oscillating viscometer 10 is provided with the holding pipe 7, the oscillating viscometer 10 measures the viscosity of the process cheese type which is before cooled in the cooling chamber 8, that is, the viscosity of the process cheese type which is held (that is, in the holding process).

However, as explained above, since the temperature of the holding pipe 7 becomes high, when the adverse effects of heat are concerned, it is preferable to measure the viscosity of the process cheese type after cooling in the cooling chamber 8 (that is, after the cooling process) by providing the oscillating viscometer 10 with the carrying out pipe 9.

In the present invention, it is possible to provide the oscillating viscometer 10 having the transducer which is immersed in the process cheese type in the holding pipe 7 or the carrying out pipe 9 so as not to contact directly the process cheese type, and to measure accurately online the viscosity of the process cheese type which is sent through the holding pipe 7 or the carrying out pipe 9.

The detected values of the oscillating viscometer 10 are sent to the control equipment 36, and displayed on the display device provided with the control equipment 36 such as a monitor, and thereby operators can monitor viscosity changes. The detected value may be the viscosity of the process cheese type which is calculated from the detected value sent from the oscillating viscometer 10, or the detected value (value of density×viscosity) sent from the oscillating viscometer 10. When the detected value is compared with a target value, in the former, the most suitable viscosity is previously set as the target value, and in the latter, the most suitable value of density×viscosity is previously fixed as the target value. The target values can be stored changeably in the recording device provided with the control equipment 36 such as a hard disk drive. In addition, the detected values can be printed by the printed device connected with the control equipment 36 such as a printer, or they may be recorded in a recorded device.

After the detected value and the target value are compared, the revolution of the frequency controlled variable speed drive 19 of the heating equipment 5 and/or the opening of the back pressure regulating valve 6 is controlled such that the detected values equals the target value, and thereby the viscosity of the process cheese type is made to be near the target viscosity. "Making the viscosity of the process cheese type to be near the target viscosity" means that two target viscosities are chosen and the viscosity of the process cheese type is made be between the two target viscosities, other than the viscosity of the process cheese type is made to equal the target viscosity.

It is preferable for the adjustment of the revolution of the frequency controlled variable speed drive 19 of the heating equipment 5 and/or the opening of the back pressure regulating valve 6 to be performed automatically by the control equipment 36. When they are controlled automatically, the revolution of the agitation bar 4 of the heating equipment 5 is controlled by calculation based on the output of the oscillating viscometer 10 which is input in the control equipment 36. In this case, when the revolution of the frequency controlled variable speed drive 19 increases (that is, the agitation intensity increases), the process cheese type becomes hard, in contrast, when the revolution decreases (that is, the agitation intensity decreases), the process cheese type becomes soft. Instead of or with the control of the revolution of the agitation bar 4, the control of the back pressure to the inside of the vessel 3 can control the hardness of the process cheese type. In this case, when the back pressure increases, the process cheese type becomes hard, and in contrast, when the back pressure decreases, the process cheese type becomes soft. However, in general, since the back pressure influences the pasteurizing temperature, when the back pressure increases and decreases rapidly, the rapid increase and decrease becomes a disturbance factor, from the view point of controlling of the pasteurizing temperature. Therefore, the back pressure should be adjusted slowly. Due to this, it is preferable for the control by the control equipment 35 to control back pressure auxiliary, in addition to control the revolution of the agitation bar 4 based on the output of the oscillating viscometer 10.

According to the present invention, since the transducer of the oscillating viscometer 10 is provided with the pipes for holding and carrying out the process cheese type so as not to contact directly the process cheese type and so as to immerse in the process cheese type, the viscosity of the melt cheese is measured online accurately without adhesion of the melt cheese to the transducer and prevention of the measurement.

In addition, since the viscosity of the melt cheese is measured online accurately, the viscosity of the process cheese type in the holding process or after the cooling process is detected on real time, the production conditions are adequately controlled. That is, a problem of time lag, which is caused in an offline viscosity measurement, can be solved, and the viscosity and quality of process cheese type can be stabilized.

In addition, the agitation intensity of the agitation bar 4 and/or the back pressure in the vessel 3 is adjusted such that an accurate detected value which is measured online becomes near a target value which is set in advance, and the agitation intensity of the agitation bar 4 and/or the back pressure in the vessel 3 is controlled automatically such that the viscosity of the process cheese type in the holding process or after cooling process becomes near a target viscosity, Thereby, a process cheese type having a target viscosity is always produced, and the viscosity and quality of a process cheese type is more stabilized.

In the embodiment, a direct heating emulsification equipment, in which steam is directly blown to cheese and the cheese is heated, is explained. However, an indirect heating emulsification equipment, in which cheese is heated and cooled by a heat transfer wall, is also used. In other words, since the indirect heating emulsification equipment comprises a heating equipment having a agitation bar similarly in the direct heating emulsification equipment, the viscosity of process cheese type is controlled by adjusting the revolution of the agitation bar and the back pressure using a valve provided at the downstream relative to the heating equipment.

The present invention will be explained in more detail with reference to an Example and a Comparative Example.

EXAMPLE

Process cheese was produced using the continuous production equipment shown in FIG. 1.

57 parts by mass of Cheddar cheese made in Australia, 28 parts by mass of Cheddar cheese made in New Zealand, 2.1 parts by mass of sodium phosphate, and 12.9 parts by mass of additional water were put into the kneader, and they were kneaded for 5 to 10 minutes so as to be uniform.

The kneaded ingredients were sent to the heating equipment, and emulsified under conditions in which a heating temperature was 85° C., a back pressure (initial target value) was 75 kPa, and a revolution of the agitation bar is 700 rpm.

The emulsified process cheese was sent to the cooling chamber, and cooled to 80° C. at a vacuum of −50 kPa. After that, in the way to transference of the process cheese through the carrying out pipe, the viscosity thereof was measured by an oscillating viscometer (marketed by CBC Materials Co., Ltd.; FMV80A-PST Type). However, as the agitation bar of the oscillating viscometer, the agitation bar which was stored in a mold form made of polytetrafluoroethylene (TEFLON®) was used.

Since the viscometer belongs to a torsional oscillation system, the value of density×viscosity was measured and is shown. As a result of preliminary examinations, the target value of the process cheese after melting was set to be 2,300. The revolution of the frequency controlled variable speed drive for driving the agitation bar and the opening of the back pressure regulating valve were controlled automatically such that the detected value measured by the oscillating viscometer becomes near the target value. The continuous production equipment was started to operate with the initial revolution and back pressure of 700 rpm and 75 kPa, respectively. After five minutes, when the equipment was in stable operating conditions, auto-control was started. When the detected value did not equal the target value, first the revolution was changed. Nevertheless, when the detected value did not reach an adjusted range of the target value, the back pressure was adjusted such that the detected value became the target value.

When the detected value of density×viscosity is larger than the target value, the process cheese is overemulsified. The detected value decreases by decreasing the revolution and adequate emulsification was recovered. When the detected value of density×viscosity is smaller than the target value, the process cheese is inadequately emulsified and mixing and melting of the solid content are not proceeded. Therefore, emulsification is facilitated by increasing the revolution. The adjusted range of the revolution was set to a range from 500 to 800 rpm. When the detected value did not equal the target value in the adjuster range of the revolution, the back pressure was adjusted. When the detected value of density×viscosity is larger than the target value, since the back pressure was high and the process cheese was in hard emulsification melt conditions, adequate emulsification was recovered by decreasing the back pressure. When the detected value of density×viscosity is smaller than the target value, since the cheese contents were heated nonuniformly, and heating was not proceeded uniformly, insufficient emulsification was generated. Therefore, the back pressure was controlled to increase and heating was performed uniformly such that the detected value becomes the target value. The adjusted range of the back pressure was set to a range from 50 kPa to 100 kPa. Moreover, the back pressure was measured by the pressure gauge 24, and input online to the control equipment 36.

As a result of process cheese being continuously produced while auto-control was performed, process cheese which had extremely stable properties, that is, process cheese having the detected value of density×viscosity in a range of 2,300±100, was produced.

COMPARATIVE EXAMPLE

Instead of the oscillating viscometer, the viscosity of process cheese was examined based on a differential pressure measurement.

In the continuous production equipment shown in FIG. 1, two holes, which were arranged perpendicularly, were formed in the sidewall of the cooling chamber 8. With the two holes, both ends of a pipe were provided, a pump was provided with the pipe, and thereby a by-pass line in a perpendicular direction was formed. Then, two pressure gauges were provided with the by-pass line, and differential pressure was measured, and thereby the viscosity of cheese in the cooling chamber was evaluated.

However, since variation of the differential pressure during operation is large, and the differential pressure was not stable, this method was not suitable for monitoring the viscosity of cheese. In addition, it was impossible to utilize the differential pressure for auto-control.

Industrial Applicability

According to the present invention, since the transducer of the oscillating viscometer is provided with the pipes for holding and carrying out the process cheese type so as not to contact directly the process cheese type, and so as to immerse in the process cheese type, the viscosity of the melted cheese is measured online accurately without obstruction of the measurement due to adhesion of the melted cheese to the transducer. It is preferable for the transducer and the process cheese type to contact indirectly via the coating material.

In addition, since the viscosity of the melt cheese is measured online accurately, the viscosity of the process cheese type in the holding process or after the cooling process is detected in real time, and the production conditions are adequately controlled. That is a problem of time lag caused in an offline viscosity measurement can be solved, and the viscosity and quality of process cheese type can be stabilized.

In addition, the agitation intensity of the agitation bar and/or the back pressure in the vessel is adjusted such that an accurate detected value which is measured online becomes near a target value which is set in advance, and the agitation intensity of the agitation bar and/or the back pressure in the vessel is controlled automatically such that the viscosity of the process cheese type in the holding process or after cooling process becomes near a target viscosity. Thereby, process cheese type having a target viscosity is always produced, and the viscosity and quality of process cheese type is more stabilized.

What is claimed is:

1. A continuous emulsification process for a type of process cheese in which a series is continuously conducted, which comprises a heating process in which a type of process cheese is agitated at any agitation intensity using an agitation device provided in a vessel while the type of process cheese is heated in the vessel applied with certain back pressure to emulsify, a holding process in which the heated emulsified type of process cheese is held at a fixed time while the heated emulsified type of process cheese is flowed into a pipe, and a cooling process in which the temperature of the heated emulsified type of process cheese after the holding process is decreased, wherein a transducer of an oscillating viscometer, which is put into a mold form made of fluorocarbon resin is immersed in the emulsified type of process cheese during the holding process or after the cooling process, and viscosity of the emulsified type of process cheese is detected; and wherein agitation intensity of the agitation device and/or back pressure applied to the vessel in the heating process is adjusted such that the viscosity of the emulsified type of process cheese detected by the immersed transducer becomes near a target value which is set in advance, and thereby, production conditions are controlled automatically and the type of process cheese is emulsified such that the viscosity of the process cheese during the holding process or after the cooling process becomes near the target viscosity.

2. A continuous production method for a type of process cheese in which a type of process cheese ingredients are kneaded, the kneaded type of process cheese ingredients are transferred to a vessel applied with certain back pressure, the type of process cheese in the vessel is agitated and emulsified with any agitation intensity using an agitation device provided to the vessel while heating in the vessel, the heated emulsified type of process cheese is held by flowing in a pipe at a certain period, the temperature of the heated emulsified type of process cheese after flowing in the pipe at a certain period is decreased, and the type of process cheese of which the temperature is decreased is molded and filled and the type of process cheese is produced, wherein a transducer of an oscillating viscometer, which is put into a mold form made of fluorocarbon resin, is immersed in the type of process cheese during being held in the pipe or after decreasing the temperature and viscosity of the emulsified type of process cheese is detected; and wherein agitation intensity of the agitation device and/or back pressure applied to the vessel during heating is adjusted such that the viscosity of the emulsified type of process cheese detected by the immersed transducer becomes near a set point which is set in advance, and thereby production conditions are controlled automatically so that the viscosity of the type of process cheese during being held in the pipe or after decreasing the temperature becomes near the target viscosity.

* * * * *